US011291769B1

(12) United States Patent
Rinehart

(10) Patent No.: US 11,291,769 B1
(45) Date of Patent: Apr. 5, 2022

(54) SYSTEMS AND METHODS FOR REGULATING FLUID INFUSION IN A PATIENT

(71) Applicant: Perceptive Medical Inc., Newport Beach, CA (US)

(72) Inventor: Joseph Rinehart, Newport Beach, CA (US)

(73) Assignee: Perceptive Medical Inc., Newport Beach, CA (US)

(*) Notice: Subject to any disclaimer, the term of this patent is extended or adjusted under 35 U.S.C. 154(b) by 0 days.

(21) Appl. No.: 17/365,730

(22) Filed: Jul. 1, 2021

Related U.S. Application Data

(60) Provisional application No. 63/199,034, filed on Dec. 3, 2020.

(51) Int. Cl.
*A61M 5/172* (2006.01)
*G16H 10/60* (2018.01)
*G16H 50/70* (2018.01)
*G16H 40/63* (2018.01)
*G16H 20/17* (2018.01)
*G16H 40/40* (2018.01)
*G05B 15/02* (2006.01)

(52) U.S. Cl.
CPC ........... *A61M 5/1723* (2013.01); *G05B 15/02* (2013.01); *G16H 10/60* (2018.01); *G16H 20/17* (2018.01); *G16H 40/40* (2018.01); *G16H 40/63* (2018.01); *G16H 50/70* (2018.01); *A61M 2005/1726* (2013.01); *A61M 2205/18* (2013.01); *A61M 2205/3334* (2013.01); *A61M 2205/50* (2013.01); *A61M 2205/52* (2013.01); *A61M 2230/30* (2013.01)

(58) Field of Classification Search
CPC ........ G16H 20/17; G16H 10/60; G16H 20/10; G16H 40/67; G16H 50/20; G16H 10/65; A61B 5/0002; A61B 5/0205; A61M 5/1723
See application file for complete search history.

(56) References Cited

U.S. PATENT DOCUMENTS 8,025,634 B1 9/2011 Moubayed et al.
8,617,135 B2 12/2013 Rinehart et al.
(Continued)

FOREIGN PATENT DOCUMENTS

CA 2838827 A1 7/2012
CA 2838831 A1 7/2012
(Continued)

OTHER PUBLICATIONS

Preview-translation of CN-106730110 obtained fron Innovation Q-IP.com. (Year: 2017).*
(Continued)

*Primary Examiner* — Manuel A Mendez
(74) *Attorney, Agent, or Firm* — Ryan Dean; Umberg Zipser LLP

(57) ABSTRACT

Closed-loop systems and methods are described herein for regulating a flow of medication being intermittently infused to a patient based on one or more vital signs. The dosage rate of the medication can be adjusted periodically as needed to ensure the patient's vital sign remains with a target range. Various safeguards can be used to ensure the safety and efficacy of the closed-loop systems and methods.

26 Claims, 7 Drawing Sheets

(56) References Cited

U.S. PATENT DOCUMENTS

| | | | |
|---|---|---|---|
| 9,022,974 | B2 | 5/2015 | Rinehart et al. |
| 10,434,255 | B2 | 10/2019 | Rinehart et al. |
| 10,512,722 | B2 | 12/2019 | Rinehart et al. |
| 2010/0036310 | A1 | 2/2010 | Hillman |
| 2011/0288380 | A1 | 11/2011 | Inciardi et al. |
| 2012/0179007 | A1 | 7/2012 | Rinehart et al. |
| 2012/0179093 | A1 | 7/2012 | Rinehart et al. |
| 2012/0179135 | A1 | 7/2012 | Rinehart et al. |
| 2012/0179136 | A1 | 7/2012 | Rinehart et al. |
| 2013/0296823 | A1 | 11/2013 | Melker et al. |
| 2014/0081201 | A1 | 3/2014 | Rinehart et al. |
| 2014/0188072 | A1 | 7/2014 | Rinehart et al. |
| 2015/0209514 | A1 | 7/2015 | Rinehart et al. |
| 2020/0001009 | A1 | 1/2020 | Rinehart et al. |
| 2020/0121851 | A1 | 4/2020 | Rinehart et al. |
| 2021/0244882 | A1 | 8/2021 | Rinehart et al. |

FOREIGN PATENT DOCUMENTS

| | | | |
|---|---|---|---|
| CA | 2838834 | A1 | 7/2012 |
| CA | 2838835 | A1 | 7/2012 |
| CA | 3123171 | A1 | 7/2012 |
| CN | 106730110 | A * | 5/2017 |
| CN | 106730110 | A | 5/2017 |
| EP | 2663225 | A2 | 11/2013 |
| EP | 2663344 | A2 | 11/2013 |
| EP | 2700358 | A2 | 2/2014 |
| EP | 2663224 | A4 | 1/2017 |
| EP | 2663349 | A4 | 1/2017 |
| WO | 2012097135 | A2 | 7/2012 |
| WO | 2012097138 | A1 | 7/2012 |
| WO | 2012097141 | A2 | 7/2012 |
| WO | 2012097129 | A3 | 11/2012 |
| WO | 2019122357 | A1 | 6/2019 |
| WO | 2021159083 | A1 | 8/2021 |

OTHER PUBLICATIONS

Gorges et al., A tool predicting future mean arterial blood pressure values improves the titration of vasoactive drugs, Journal of Clinical Monitoring and Computing (2010) 24:223-235, DOI: 10.1007/s10877-010-9238-0.

Joosten, et al., Automated closed-loop versus manually controlled norepinephrine infusion in patients undergoing intermediate- to high-risk abdominal surgery: a randomised controlled trial, British Journal of Anesthesia, Jan. 2021., 126(1):210-218. doi: 10.1016/j.bja.2020.08.051. Epub Oct. 8, 2020.

Joosten, et al., Automated Titration of Vasopressor Infusion Using a Closed-loop Controller: In Vivo Feasibility Study Using a Swine Model, Anesthesiology, Mar. 2019, 130(3):394-403, doi: 10.1097/ALN.0000000000002581.

Joosten, et al., Feasibility of closed-loop titration of norepinephrine infusion in patients undergoing moderate- and high-risk surgery, British Journal of Anesthesiology, Oct. 2019., 123(4):430-438. doi: 10.1016/j.bja.2019.04.064. Epub Jun. 27, 2019.

Joosten, et al., Feasibility of computer-assisted vasopressor infusion using continuous non-invasive blood pressure monitoring in high-risk patients undergoing renal transplant surgery, Anesthesia, Critical Care and Pain Medicine, Oct. 2020, 39(5):623-624. doi: 10.1016/j.accpm.2019.12.011. Epub Apr. 5, 2020.

Rinehart, et al., Blood pressure variability in surgical and intensive care patients: Is there a potential for closed-loop vasopressor administration?, Anesthesia, Critical Care and Pain Medicine, 2018, https://doi.org/10.1016/j,accpm.2018.11.009.

Rinehart, et al., Closed-loop vasopressor control: in-silico study of robustness against pharmacodynamic variability, Journal of Clinical Monitoring and Computing, 2018, https://doi.org/10.1007/s10877-018-0234-0.

Rinehart, et al., Feasibility of automated titration of vasopressor infusions using a novel closed-loop controller, Journal of Clinical Monitoring and Computing, 2017, DOI 10.1007/s10877-017-9981-6.

Sia et al., Closed-loop double-vasopressor automated system to treat hypotension during spinal anaesthesia for caesarean section: a preliminary study, Anaesthesia 2012, 67, 1348-1355, doi:10.1111/anae.12000.

Sng et al., Closed-loop double-vasopressor automated system vs manual bolus vasopressor to treat hypotension during spinal anaesthesia for caesarean section: a randomised controlled trial, Anaesthesia 2014, 69, 37-45, doi:10.1111/anae.12460.

Joosten, et al., Feasibility of closed-loop titration of norepinephrine infusion in patients undergoing moderate- and high-risk surgery, British Journal of Anaesthesia, Cardiovascular, Oct. 1, 2019, vol. 123, Issue4, pp. 430-438, doi: 10.1016/j.bja.2019.04.064.

Rinehart, et al., Closed-Loop Control of Vasopressor Administration in Patients Undergoing Cardiac Revascularization Surgery, Journal of Cardiothoracic and Vascular Anesthesia, Nov. 1, 2020, vol. 34, Issue 11, pp. 3081-3085, DOI:https://doi.org/10.1053/j.jvca.2020.03.038.

Korea Intellectual Property Office, International Search Report and Written Opinion, dated Feb. 4, 2022.

* cited by examiner

SYSTEMS AND METHODS FOR REGULATING FLUID INFUSION IN A PATIENT

This application claims priority to U.S. provisional application having Ser. No. 63/199,034 filed on Dec. 3, 2020. This and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is closed-loop fluid infusion systems and methods, and in particular, systems and methods for use with intravenous fluid infusion pumps.

BACKGROUND

The following description includes information that may be useful in understanding the present invention. It is not an admission that any of the information provided herein is prior art or relevant to the presently claimed invention, or that any publication specifically or implicitly referenced is prior art.

Maintaining a patient's blood pressure or other vitals can be difficult, and poor control can affect the patient's well-being. During operations, low blood pressure can occur frequently and has been correlated to negatively affect patient outcomes. For example, patients having a mean arterial pressure (MAP) less than 55-65 mmHg for just one minute during an operation have a higher risk of death than those whose blood pressure remains stable.

Unfortunately, manual control of medication to maintain blood pressure and other vitals during surgery can be challenging. Optimization of blood pressure or other vitals requires taking repeated measurements of a patient's vital sign, and making frequent, manual adjustments of medication dosage rates. As this most typically requires continuous attention of a medical professional, this can be cost prohibitive and difficult to achieve.

FIG. 1 illustrates a typical workflow for manually maintaining a patient's vital sign. A nurse or other medical professional reviews the patient's vital sign such as on a monitor and then manually adjusts a dosage rate of the medication to the patient. As medical professionals often care for multiple patients at a time, each patient's vital signs are checked periodically but not frequently, which misses the opportunity for additional corrections. In addition, the adjustments can be arbitrary based on snapshot views of the patient's vital sign.

For blood pressure, such manual control often leads to the patient being outside of the target range for the patient for a significant amount of time. For example, one study found that manual control of blood pressure resulted in patients being outside of the target range more than 50% of the time, with the patients being in hypotension (below the target range) 10%-15% of the time and in hypertension (above the target range) 30%-40% of the time.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, there is still a need for closed-loop systems and methods for continuous optimization of the dose rate of a medication given to a patient over time.

SUMMARY OF THE INVENTION

The inventive subject matter provides apparatus, systems and methods for regulating a flow of medication or other fluid to a patient. Information about a patient such as one or more vital signs can be received from at least one source including, for example, a transducer or other sensor. A target value and/or range for one or more of the vital signs can be received. In one example, the target value and/or range can be inputted using a graphical user interface. An initial dosage rate of the medication or other fluid to be administered to the patient can also be received.

Such vital signs could include, for example, a mean arterial pressure of a patient, but could also comprise any other vital sign that can be controlled through intermittent infusion of the medication, such as by using an intravenous infusion device.

Based on information received about the patient, such as the one or more vital signs, a first control algorithm can be used to generate a revised dosage rate for delivery of the medication or other fluid to the patient. The first control algorithm determines a differential value by comparing a value of the first vital sign with the target value, and then generating the revised dosage rate as a function of the initial (first) or current dosage rate and the differential value. Once generated, medication can then be delivered to the patient according to the revised dosage rate. The first control algorithm can be configured to continually monitor the patient's information (e.g., one or more vital signs), and make on-going corrections to the dosage rate of the medication or other fluid as needed to keep the patient's vital sign within a target range (i.e., a predetermined range from the target value of the vital sign).

In another embodiment, a non-transitory computer readable medium stores a computer program that includes commands to cause a processor to perform a method for regulating a flow of medication to a patient. The program can receive information concerning (i) a first vital sign of the patient from a first source and (ii) a target value for the first vital sign. An initial or current dosage rate of a medication administered to the patient can also be received.

The processor can run the computer program and compare a current value of the first vital sign to the target value or range to determine a differential value, and then generate a revised dosage rate for delivery of the medication to the patient as a function of the initial (first) or current dosage rate and the differential value. Once generated, the medication can be delivered to the patient according to the revised dosage rate.

Various objects, features, aspects and advantages of the inventive subject matter will become more apparent from the following detailed description of preferred embodiments, along with the accompanying drawing figures in which like numerals represent like components.

DETAILED DESCRIPTION

Throughout the following discussion, numerous references may be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Figure 1:
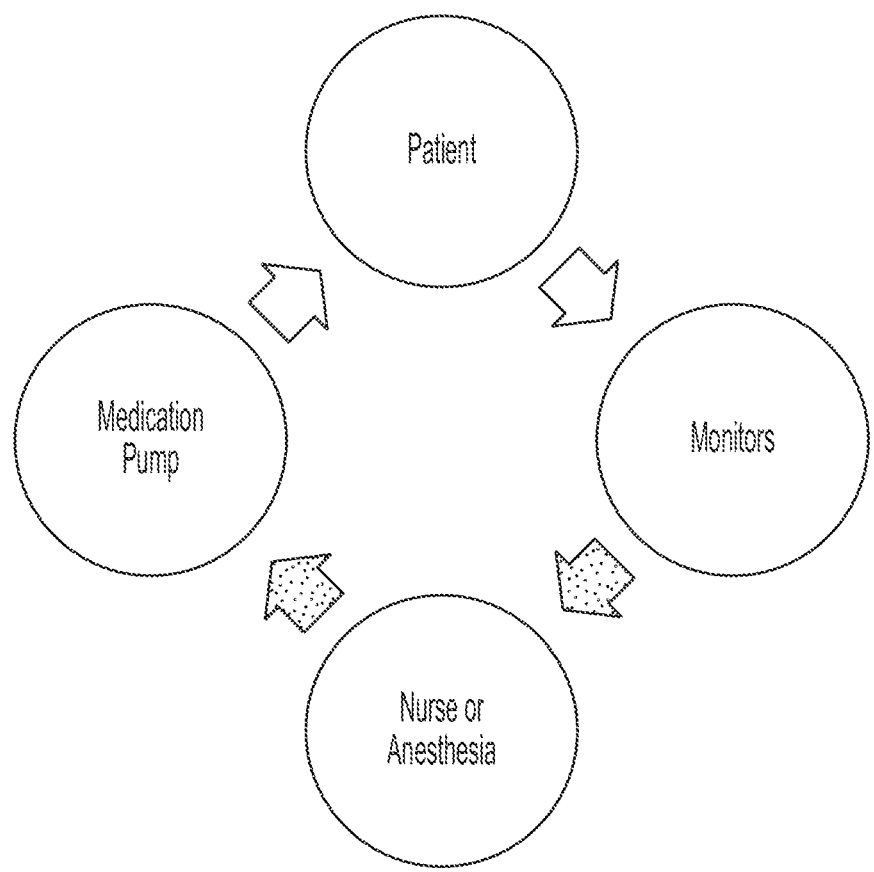
FIG. 1 illustrates a prior art flow chart for manual regulation of a patient's vital sign.
Figure 2:
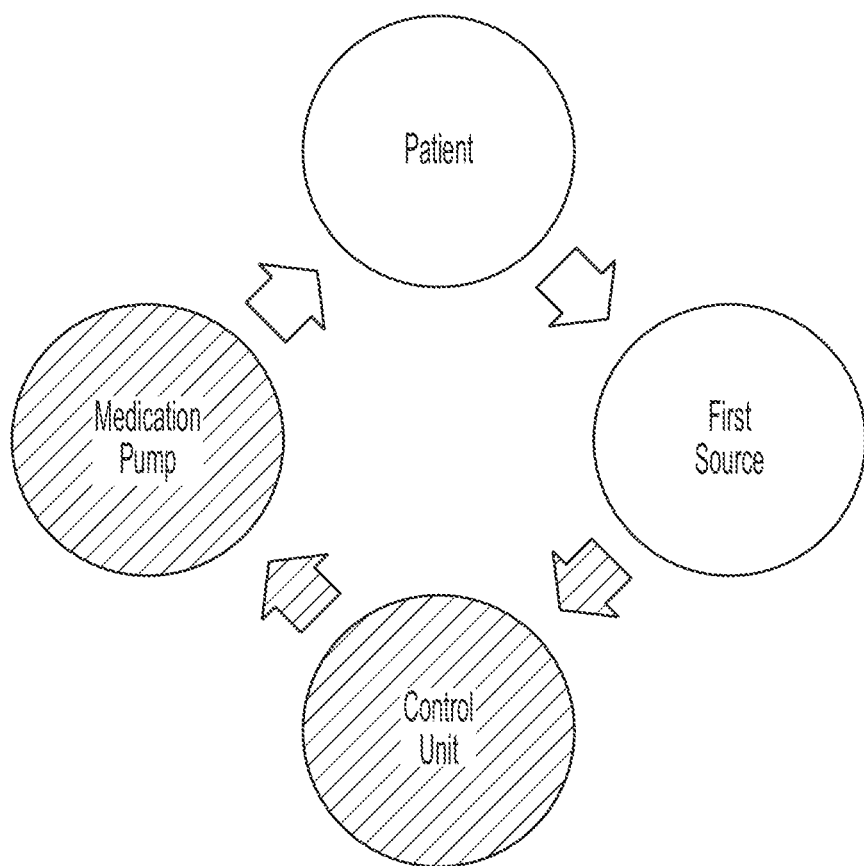
FIG. 2 illustrates a flow chart for automatic regulation of a patient's vital sign.

FIG. 2 illustrates a simplified flowchart for automatic regulation of a vital sign of a patient using automated adjustments of a dosage rate of a medication to the patient based on changes to the patient's one or more vital signs being monitored.

Figure 3:
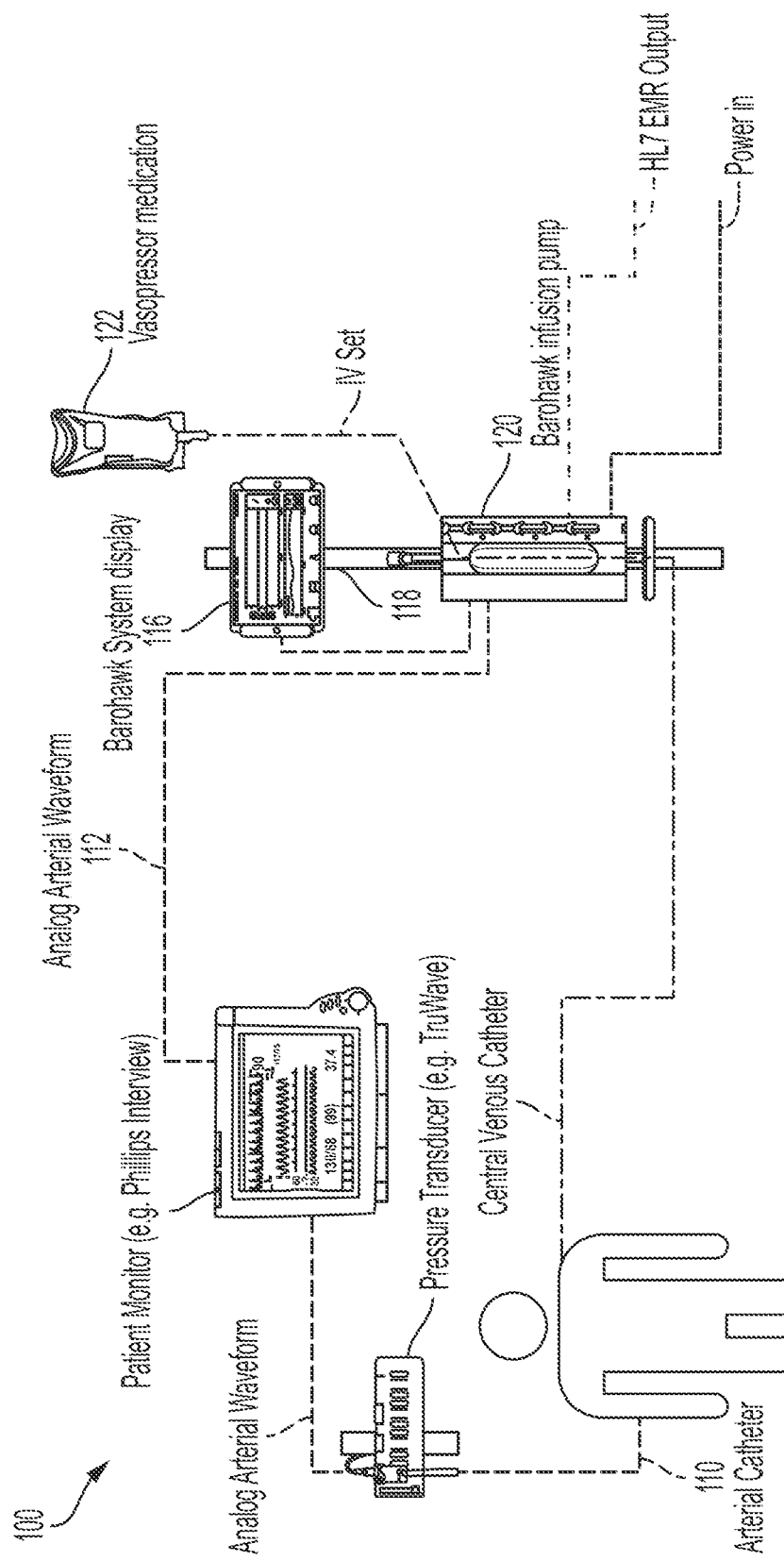
FIG. 3 illustrates a diagram of one embodiment of a method for regulating a flow of medication to a patient.

FIG. 3 illustrates a first embodiment of a method 100 for regulating a flow of medication 122 to a patient 114. A target value for a first vital sign and an initial (first) or current dosage rate of a medication 122 to be administered to a patient 114 can be received, such as via an input to a graphical user interface 116.

Information 112 concerning the first vital sign of the patient 114 can be received from a first source 110 directly such as from the sensor or indirectly such as from a patient monitoring device. Based on the received information 112, a revised dosage rate 118 can be generated using a first control algorithm. The medication 122 can then be delivered to the patient 114 according to the revised dosage rate such as with an infusion pump 120. In this manner, the first vital sign of the patient 114 can be periodically and continuously monitored and adjustments to the dosage rate of the medication 122 can be made depending on the difference between the first vital sign and the target value or range as well as other factors. In some embodiments, the adjustment to the dosage rate may consider the initial (first) or current dosage rate, a differential value between the current vital sign and the target value or range, and a scalar rate associated with the medication 122. Although a vasopressor is shown as the medication, it is contemplated that the systems and methods described herein can be used with any other medications that can be used to control one or more vitals of a patient and are intermittently infused to a patient.

In some contemplated embodiments, a processor runs the first control algorithm which compares a value of the patient's first vital sign with the target value or range to determine a differential value, and then generates the revised dosage rate as a function of the initial (first) or current dosage rate and the differential value.

As one example, it is contemplated that the systems and methods herein can be used to regulate a blood pressure of a patient, such as by controlling a dosage rate of a vasopressor intermittently administered to the patient. In such embodiments, it is contemplated that the first vital sign may comprise a mean arterial pressure (MAP) of the patient, which could be measured using a transducer attached to the patient. The systems and methods are preferably configured to monitor and track the MAP of the patient, and utilize the first control algorithm to generate revised dosage rates in response to changes in the MAP of the patient to thereby maintain the first vital sign of the patient within a target range of the of the target value (e.g., within 5 mmHg). The revised dosage rate can be transmitted to an IV infusion device, for example, which can then change the dosage rate of the medication being administered to the patient.

It is further contemplated that additional safeguards can be used to help ensure the systems and methods described herein are not concealing that a patient's condition is worsening by maintaining the patient's blood pressure or other vital sign such as by continuing to increase the dosage rate of the medication. In one such example, it is contemplated that the initial (first) dosage rate, a set of prior dosage rates, a current dosage rate (if applicable), and the revised dosage rate can be stored in a memory communicatively coupled with the processor, and the set of stored dosage rates of the medication for the patient can be analyzed by the processor. If a rate of change of the dosage rate of the medication over a set time period exceeds a predetermined threshold, an alarm command can be generated to notify the medical team of the potential worsening condition of the patient despite the patient's vital sign remaining in the target range.

Additionally, or alternatively, another safeguard that can be used is to require that a set time period has elapsed between dosage rate changes before making further adjustments to the dosage rate of the medication. For example, it is contemplated that in the step of generating the revised dosage rate, a first time period is determined that is measured as the time elapsed since the last dosage rate change of the medication. Then, if the first time period is less than a minimum time period, the dosage rate is not changed. However, if the first time period is greater than or equal to the minimum time period, the revised dosage rate can be set as the initial (first) or current dosage rate of the medication for the patient.

In such embodiments, it is preferred that the minimum time period is greater than or equal to a line lag of the medication being delivered, which can be calculated by understanding the length of tubing through which the medication must flow from the medication source to the patient, and the flow rate of the medication through the tubing. General estimations can also work. It is important that the systems and methods do not alter the dosage rate until the patient is actually receiving medication at the prior dosage rate. Because the line lag can be one to two minutes or more depending on the circumstances, this safeguard helps ensure that the systems and methods do not overcompensate by adjusting the dosage rate of the medication without accounting for the line lag but instead allow time for the change in dosage rate to take effect.

To further ensure the closed-loop systems and methods are safe for the patient, it is preferred that minimum and maximum dosage rates of the medication are inputted for the patient. Where this has not occurred, it is contemplated that the systems and methods could prompt the medical professional for the information or could have default values that could be used that may depend on the medication being delivered to the patient.

In such embodiments, it is contemplated that the first control algorithm can further determine whether the revised dosage rate is greater than the minimum dosage rate and less than the maximum dosage rate. If not, it is contemplated that the initial (first) or current dosage rate can be maintained (not adjusted) and the medication can be delivered to the patient according to the initial (first) or current dosage rate. In such instances, it is further contemplated that an alarm status can be generated to alert the medical professional to the issue. Alternatively, it is contemplated that the revised dosage rate could be adjusted from the current dosage rate to the minimum or maximum dosage rate, as applicable, and the alarm status can be generated.

In still further embodiments, it is contemplated that the systems and methods can further ensure that the dosage rate is not changed by more than a set amount (limit change threshold) at any one adjustment. For example, it is contemplated that the first control algorithm can calculate a difference between the revised dosage rate and the initial (first) or current dosage rate prior to delivering the medication to the patient according to the revised dosage rate. If the difference between the two dosage rates exceeds the limit change threshold, the revised dosage rate can instead be set to the limit change threshold plus the initial (first) or current dosage rate. Thus, in such embodiments, while the dosage rate will be changed, it will only be adjusted by the value of the limit change threshold. In such instances, it is further contemplated that an alarm status could be generated to alert the medical professional to the issue.

It is further contemplated that the first vital sign could be independently monitored from a second source in addition to the first source. Information about the first vital sign can be received from the second source and the received information from the second source can be compared with information received about the first vital sign from the first source. If the difference between the information of the first and second sources exceeds a predetermined threshold, an alarm command can be generated. Whether the units of the measured vital sign are different between that measured by the first and second sources, it is contemplated that the received information from one of the sources can be converted to allow a comparison of the values. For example, for blood pressure monitoring, it is contemplated that a first source could monitoring the MAP of the patient while the second source could monitor the systolic blood pressure (SBP) and diastolic blood pressure (DBP) of the patient. In such circumstances, the systolic blood pressure could be converted to MAP using the following equation:

$$MAP = \frac{SBP + 2*(DBP)}{3}$$

In addition to the first vital sign, it is contemplated that other vital signs of the patient could be monitored including, for example, oxygen saturation levels ($SpO_2$), body temperature, and electrical signals from the heart (EKG). Additionally, or alternatively, perfusion and/or metabolic activity in the patient could also be monitored.

As but one example, in the case of monitoring a blood pressure of the patient, it is contemplated that the first source can be a transducer attached to the patient and the second source could be a blood pressure monitor configured to monitor a systolic blood pressure.

In another aspect, a non-transitory computer readable medium is provided in which a computer program is stored. Preferably, the computer program includes commands that cause a processor of a server to perform a method for regulating a flow of medication to a patient. Thus, for example, an intravenous infusion device can comprise a processor communicatively coupled with the non-transitory computer readable medium where the computer program is stored, which may include or comprise the first control algorithm discussed above. The intravenous infusion device could be a control unit to monitor and calculate dosage rates or a separate control unit could communicate with the intravenous infusion device to control the dosage rate of a medication to the patient.

The computer program can be configured to receive, via the control unit, information concerning a first vital sign of a patient from a first source. A target value of the first vital sign and an initial (first) or current dosage rate of a medication to be or being administered to the patient can also be received, such as via a GUI connected to the control unit.

Based on the information received, the processor of the control unit can run the computer program and compare a value of the first vital sign with the target value or range to determine a differential value. A revised dosage rate can then be generated and transmitted to the infusion device for delivery of the medication to the patient based on the initial (first) or current dosage rate and the differential value, and the current dosage rate and can be adjusted to the revised dosage rate.

The medication can then be delivered to the patient according to the revised dosage rate using the infusion device.

In some embodiments, it is contemplated that the first vital sign can comprise a mean arterial pressure of the patient, and the medication can comprise a vasopressor. In such embodiments, it is contemplated that the first source can be a transducer attached to the patient or another sensor capable of measuring MAP or other indicator of the blood pressure of the patient.

The first dosage rate, prior dosage rates, a current dosage rate if applicable, and the revised dosage rate can be stored in the same or different non-transitory computer readable medium. A set of the stored dosage rates of the medication can be analyzed and an alarm command can be generated if a rate of change of the dosage rates over a specific time period exceeds a predetermined threshold.

As discussed above, various other safeguards can be implemented in the computer program to ensure that the adjustments to the dosage rate is safe for the patient. Examples include setting minimum and maximum dosage rates of the medication, limiting how frequently dosage rates can be adjusted, and/or setting a maximum value for a single adjustment to the dosage rate.

Thus, for example, it is contemplated that generating the revised dosage rate includes first determining whether at least a preset amount of time or minimum time period has elapsed since the last dosage rate change, and if not, the dosage rate can remain unchanged. If the amount of elapsed time exceeds the minimum time period, the dosage rate can be adjusted. Preferably, in such embodiments, the minimum time period can be greater or equal to a line lag that exists for the medication being administered to the patient. As discussed above, this line lag is based on a length of the tubing as measured from the medication source to the patient and a flow rate of the medication through the tubing.

It is also contemplated that generating the revised dosage rate could include calculating a difference between the revised dosage rate and the initial (first) or current dosage rate. If the difference between the current and revised dosage rates exceeds a limit change threshold, the revised dosage rate can be set to the limit change threshold plus the initial (first) or current dosage rate.

Figure 7:
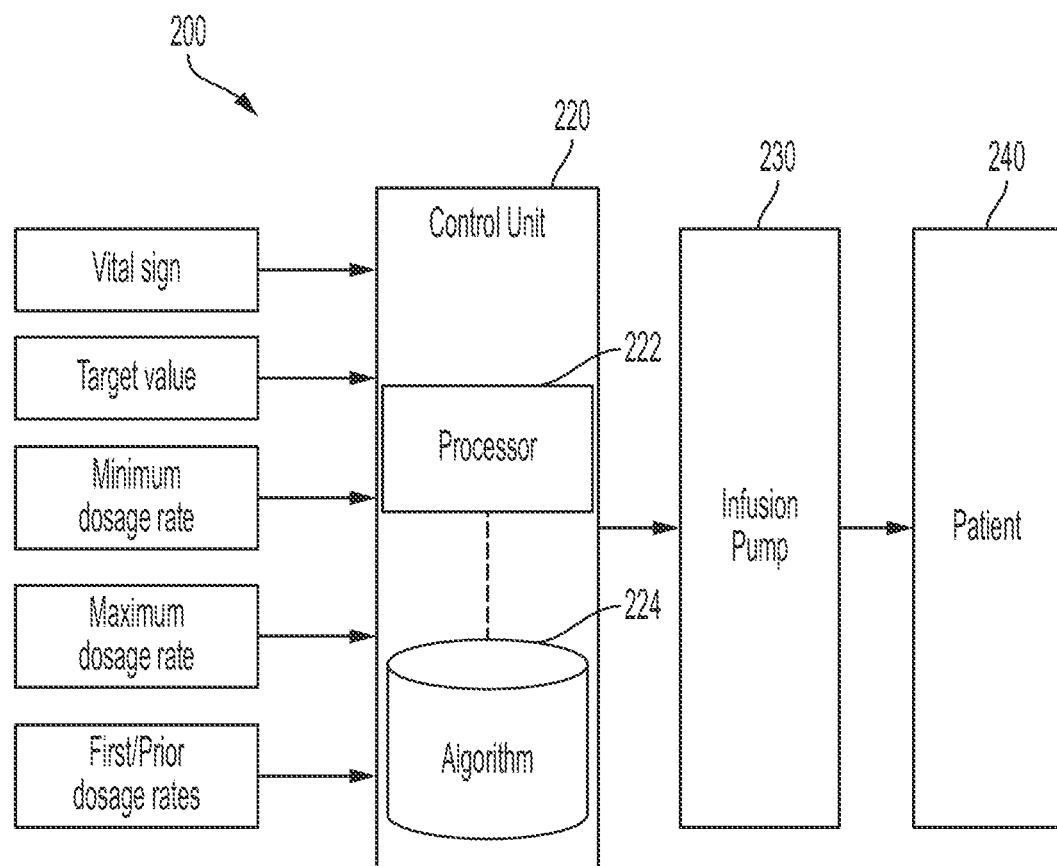
FIG. 7 illustrates one embodiment of a system for automatic regulation of a patient's vital sign.

Various systems are also contemplated for regulating a flow of medication to a patient. In FIG. 7, one embodiment of a system 200 can comprise a control unit 220 having a processor 222 communicatively coupled with a memory 224 that is configured to store a first control algorithm. The control unit 220 is configured to receive information concerning a first vital sign of a patient 240 from a first source, a target value or range for the first vital sign, and an initial (first) or current dosage rate for intermittent delivery of the medication to the patient. The medication can be delivered using an infusion device which may or may not comprise the control unit 220.

If the vital sign is outside of the target range, the control unit 220 generates a revised dosage rate for delivery of the medication to the patient 240 using the first control algorithm. The first control algorithm is programmed to compare a value of the first vital sign with the target value or range to determine a differential value, and then generate the revised dosage rate based on the initial (first) or current dosage rate and the differential value. For example, if the patient's vital sign exceeds the target value or range, the difference between the vital sign and the target value or range can be calculated (the differential). The control unit can then calculate the additional amount of medicine (increase to the dosage rate) needed to reduce the vital sign to be within the target range. This increase to the dosage rate can then be added to the current dosage rate to generate the revised dosage rate.

The control unit 220 can then send a command signal to cause the medication to be delivered via an infusion pump 230 to the patient 240 at the revised dosage rate.

In some contemplated embodiments, the first vital sign comprises a mean arterial pressure of the patient 240 and the first source comprises a transducer attached to the patient 240.

It is also contemplated that the control unit 220 can store the initial dosage rate and a history of adjustments to the dosage rate or revised dosage rates, and analyze the stored dosage rates of the medication for the patient 240. If a rate of change of the dosage rates over a certain time period exceeds a predetermined threshold, the control unit 220 can generate an alarm command.

As discussed above, various other safeguards can be implemented in the control unit 220 control algorithm to ensure that the dosage rate are safe for the patient 240. Examples include setting minimum and maximum dosage rates, limiting how frequently dosage rates are adjusted, and/or setting a maximum value for dosage rate adjustments.

Figure 4:
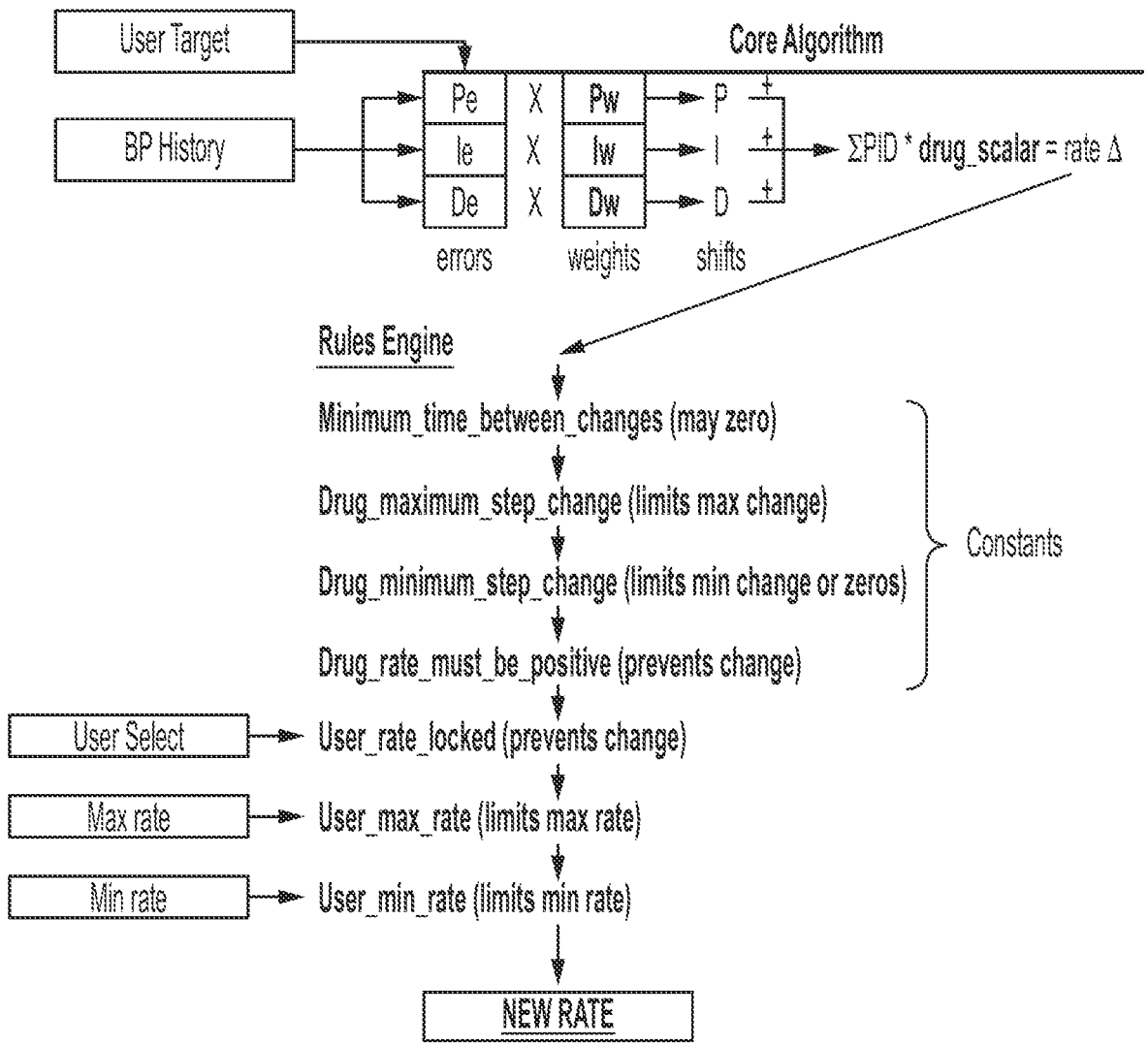
FIG. 4 illustrates an exemplary embodiment of a first control algorithm.

An exemplary embodiment of the computer software or first control algorithm is shown in FIG. 4. A PID controller can be used to determine a dosage rate change based on the target value for the vital sign, the current value of the vital sign, and optionally a blood pressure history of the patient. The resulting value can be multiplied by a drug scalar to arrive at the dosage rate change value which can then be combined with the current dosage rate to generate a revised dosage rate. The revised dosage rate can be analyzed by a rules engine to ensure the safety of the new dosage rate for the patient, such as by implementing some or all of the safeguards described above.

Figure 5:
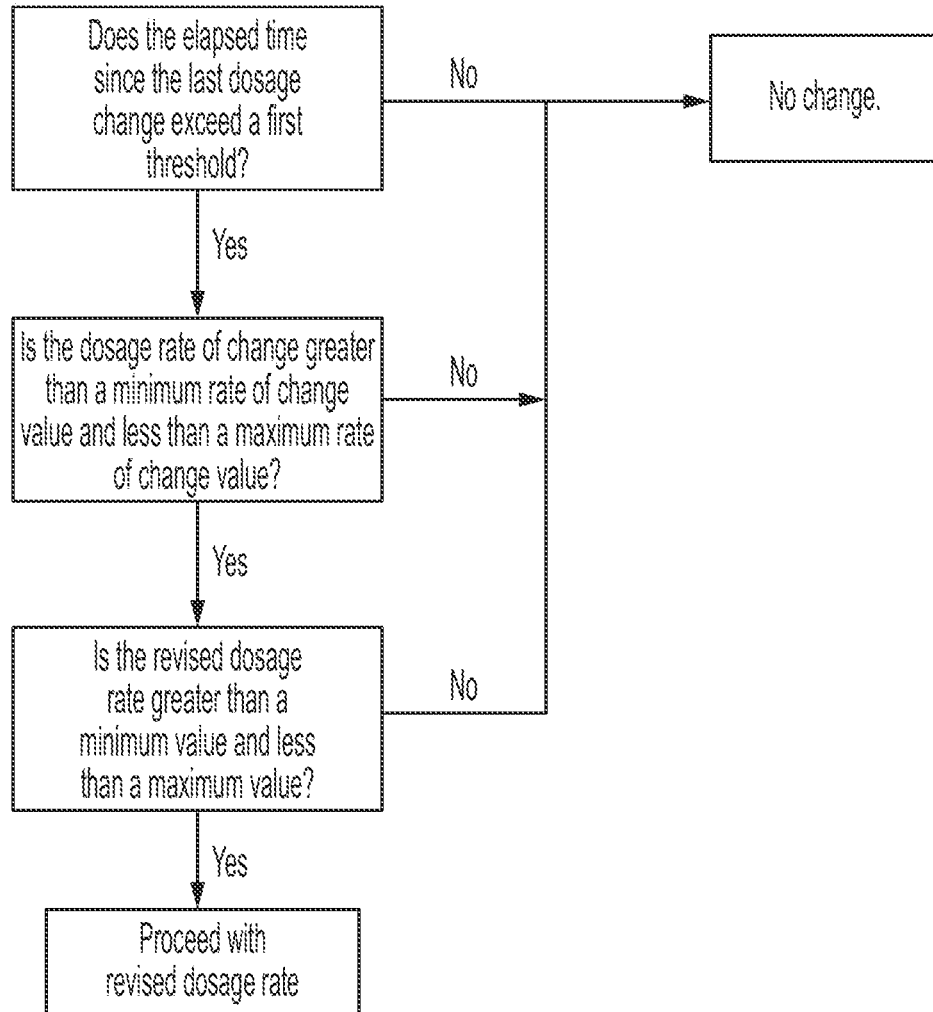
FIG. 5 illustrates an exemplary embodiment of a rules engine.

An exemplary rules engine is shown in FIG. 5. As shown, the revised dosage rate calculated using the control algorithm can be analyzed to ensure it is safe for the patient. Although shown in a specific order, it is contemplated that the order of the analyses can be varied without departing from the scope of the invention.

As shown, an elapsed time since the last dosage rate change of the medication can be monitored. When a revised dosage rate is calculated, the elapsed time can be compared with a first threshold. If the elapsed time is less than the first threshold, the dosage rate will not be adjusted (no change). If the elapsed time is greater than or equal to the first threshold, the dosage rate will be adjusted if all other programmed criteria are met.

the adjustment to the dosage rate can also be analyzed to ensure the adjustment is greater than a minimum value and less than a maximum value. This helps ensure that the adjustment is not made unless over a minimum amount such as a minimum change permitted by the infusion device. It also ensures that any adjustments to the dosage rate are gradual steps rather than a large change over a short time period. If the adjustment is between the two values, the dosage rate will be adjusted if all other programmed criteria are met. If not, the dosage rate will not be adjusted (no change).

The revised dosage rate may also be compared with minimum and maximum dosage rate values to ensure the revised dosage rate does not fall outside of these thresholds. If the revised dosage rate is between the two values, the dosage rate will be adjusted if all other programmed criteria are met. If not, the dosage rate will not be adjusted (no change).

Figure 6:
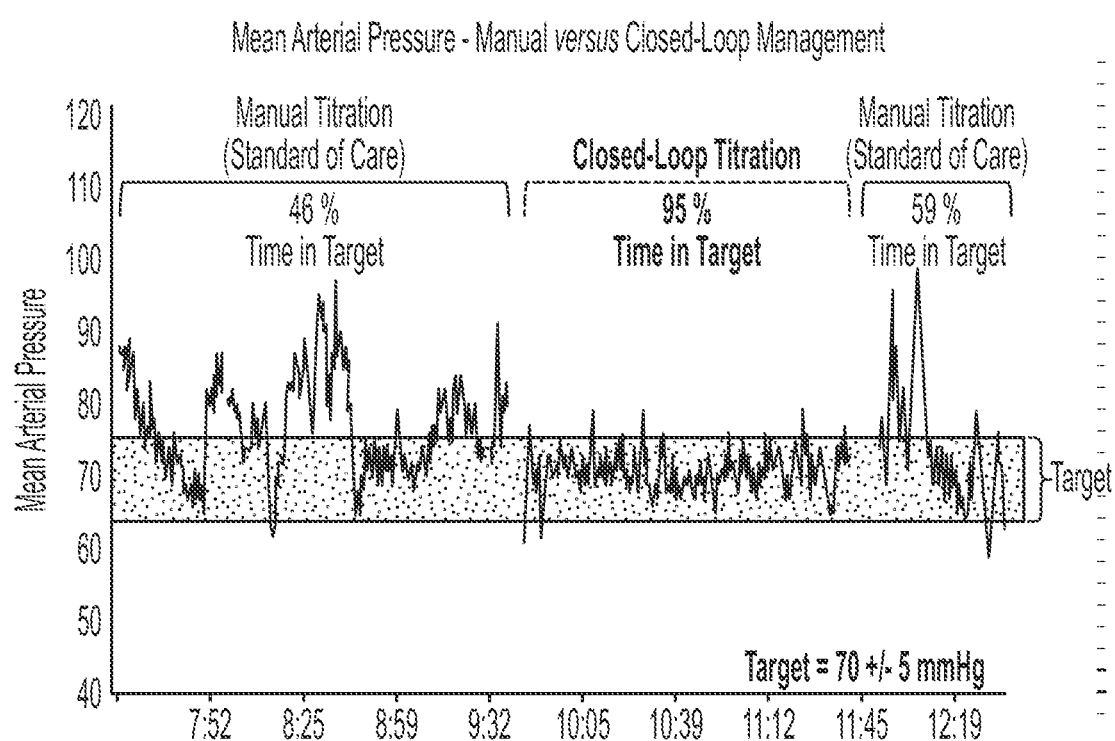
FIG. 6 illustrates an example comparing a time in target of a patient using manual control versus automated control.

FIG. 6 illustrates a comparison of manual control of a blood pressure of a patient to automated control using the closed-loop systems and methods described herein. As shown, the time in target of the automated control (95%) greatly exceeded the time in target of the manual control (46% and 59%). The time in target is calculated by determining how long the patient's blood pressure was within ±5 mmHg of the set target value for the patient over a specified time period.

The use of the closed-loop systems and methods described herein also resulted in a total dose of vasopressor in those patients using the closed-loop systems and methods being 40% lower than those patients using manual control (control group). In addition, the closed-loop system adjusted dosage rates of the vasopressor more than 1,000 times per patient compared with a median of 15 times per patient in the control group.

The percentage of intraoperative case time a patient had hypotension (defined as a MAP <90% of the patient's baseline MAP) was 1.2% for those using the closed-loop systems and methods and 21.5% for those using manual control. The percentage of intraoperative case time with a MAP <65 mmHg was also lower for those using the closed-loop system than in the control group (average of 0% vs 1.9%). Patients using the closed-loop systems and methods were also within their target MAP range (±10 mmHg of their baseline MAP value) for an average of 97.2% of the time compared with an average of 58.8% of the time for those under manual control. The percentage of time with hypertension (defined as a MAP >10 mmHg of the MAP target)

was also lower for those using the closed-loop systems and methods than those in the control group using manual control (average of 2.5% vs 12.9%).

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing measurements, quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method for regulating a flow of medication to a patient, comprising:
   receiving information representing a current value of a first vital sign of a patient from a first source;
   receiving a target value or range for the first vital sign;
   receiving and storing a first dosage rate of a medication administered to the patient;
   if the information representing the current value of the first vital sign falls outside of the target range, generating a revised dosage rate for delivery of the medication to the patient using a first control algorithm, wherein the first control algorithm includes the following steps:
      comparing the information representing the current value of the first vital sign with the target value or range to determine a differential value;
      calculating a dosage adjustment based on the differential value and a drug scalar value; and
      generating the revised dosage rate as a function of the dosage adjustment and the first dosage rate;
   delivering the medication to the patient according to the revised dosage rate;
   storing the revised dosage rate;
   analyzing a set of prior dosage rates of the medication for the patient including the first dosage rate; and
   generating an alarm command if a rate of change of the prior dosage rates over a set time period exceeds a predetermined threshold.

2. The method of claim 1, wherein the first vital sign comprises a mean arterial pressure of the patient, and wherein the first source comprises a transducer attached to the patient.

3. The method of claim 1, wherein the step of generating the revised dosage rate further comprises:
   prior to delivering the medication to the patient according to the revised dosage rate, determining whether a first time period exceeds a minimum time period, wherein the first time period is defined as an elapsed time since a last dosage rate change occurred;
   if the first time period is less than the minimum time period, setting the revised dosage rate to the first dosage rate;
   if the first time period is greater than the minimum time period, delivering the medication to the patient according to the revised dosage rate; and wherein the minimum time period is greater or equal to a line lag.

4. The method of claim 1, further comprising:
receiving a minimum dosage rate and a maximum dosage rate; and
wherein the first control algorithm further comprises:
  determining whether the revised dosage rate is greater than the minimum dosage rate and less than the maximum dosage rate; and
  if not, (i) setting the revised dosage rate to the first dosage rate, (ii) maintaining the first dosage rate and delivering the medication to the patient according to the first dosage rate, and (iii) generating an alarm status.

5. The method of claim 1, wherein the first control algorithm further comprises:
prior to delivering the medication to the patient according to the revised dosage rate, calculating a difference between the revised dosage rate and the first dosage rate; and
if the difference exceeds a limit change threshold, setting the revised dosage rate to the limit change threshold plus the first dosage rate.

6. The method of claim 1, further comprising:
receiving information concerning the first vital sign from a second source comprising a blood pressure monitor configured to monitor a systolic blood pressure of the patient;
comparing the information received concerning the first vital sign from the first and second sources;
if the difference between the first vital sign as measured from the first and second sources exceeds a predetermined threshold, generating an alarm command.

7. The method of claim 1, wherein the medication comprises a vasopressor.

8. The method of claim 7, wherein the first vital sign comprises a mean arterial pressure of the patient, and wherein the first control algorithm is configured to generate the revised dosage rate to maintain the first vital sign within 5 mmHg of the target value.

9. The method of claim 1, further comprising:
receiving a flow rate of a carrier fluid;
calculating a line lag based on the flow rate of the carrier fluid;
setting a minimum time period equal to the line lag; and
wherein the step of generating the revised dosage rate further comprises first determining whether a first time period as measured as time elapsed since a last dosage rate change exceeds the minimum time period.

10. A non-transitory computer readable medium in which a computer program is stored, wherein the computer program includes commands which cause a processor of a server to perform a method for regulating a flow of medication to a patient, the method comprising:
receiving, via a control unit, information representing a first vital sign of a patient from a first source;
receiving, via the control unit, a target value for the first vital sign;
receiving, via the control unit, a first dosage rate of a medication administered to the patient and storing the first dosage rate;
the control unit comparing a current value of the first vital sign with the target value to determine a differential value;
generating, via the control unit, a dosage adjustment based on the differential value and a drug scalar value;
generating, via the control unit, a revised dosage rate for delivery of the medication to the patient as a function of the first dosage rate and the dosage adjustment and using computer program;
storing the revised dosage rate in the non-transitory computer readable medium;
analyzing a set of dosage rates of the medication for the patient including the first dosage rate;
generating an alarm command if a rate of change of the dosage rates over a set time period exceeds a predetermined threshold; and
delivering the medication to the patient according to the revised dosage rate.

11. The non-transitory computer readable medium of claim 10, wherein the first vital sign comprises a mean arterial pressure of the patient, and wherein the first source comprises a transducer attached to the patient.

12. The non-transitory computer readable medium of claim 10, wherein the step of generating the revised dosage rate further comprises:
prior to delivering the medication to the patient according to the revised dosage rate, determining whether a first time period exceeds a minimum time period, wherein the first time period is defined as an elapsed time since a last dosage rate change occurred;
if the first time period is less than the minimum time period, setting the revised dosage rate to the first dosage rate;
if the first time period is greater than the minimum time period, delivering the medication to the patient according to the revised dosage rate; and
wherein the minimum time period is greater or equal to a line lag.

13. The non-transitory computer readable medium of claim 10, wherein the method further comprises:
receiving a minimum dosage rate and storing the minimum dosage rate in the non-transitory computer readable medium;
receiving a maximum dosage rate and storing the maximum dosage rate in the non-transitory computer readable medium; and
determining whether the revised dosage rate is greater than the minimum dosage rate and less than the maximum dosage rate; and
if not, (i) setting the revised dosage rate to the first dosage rate, (ii) delivering the medication to the patient according to the first dosage rate, and (iii) generating an alarm command.

14. The non-transitory computer readable medium of claim 10, wherein the method further comprises:
prior to delivering the medication to the patient according to the revised dosage rate, calculating a difference between the revised dosage rate and the first dosage rate; and
if the difference exceeds a limit change threshold, setting the revised dosage rate to the limit change threshold plus the first dosage rate.

15. The non-transitory computer readable medium of claim 10, wherein the method further comprises:
receiving information concerning the first vital sign from a second source comprising a blood pressure monitor configured to monitor a systolic blood pressure of the patient;
comparing the information received concerning the first vital sign from the first and second sources;

if the difference between the first vital sign as measured from the first and second sources exceeds a predetermined threshold, generating an alarm command.

16. The non-transitory computer readable medium of claim 10, wherein the medication comprises a vasopressor, and wherein the first vital sign comprises a mean arterial pressure of the patient, and wherein the first control algorithm is configured to generate the revised dosage rate to maintain the first vital sign within 5 mmHg of the target value.

17. The non-transitory computer readable medium of claim 10, wherein the method further comprises:
   receiving a flow rate of a carrier fluid;
   calculating a line lag based on the flow rate of the carrier fluid;
   setting a minimum time period equal to the line lag; and
   wherein the step of generating the revised dosage rate further comprises first determining whether a first time period as measured as time elapsed since a last dosage rate change exceeds the minimum time period.

18. A system for regulating a flow of medication to a patient, comprising:
   a control unit comprising a processor and a memory communicatively coupled with the processor, wherein the memory stores a first control algorithm;
   the control unit configured to receive information concerning a first vital sign of a patient from a first source;
   the control unit further configured to receive a target value or range for the first vital sign and a first dosage rate for delivery of a medication to the patient;
   the control unit generating a revised dosage rate for delivery of the medication to the patient using a first control algorithm;
   the control unit sending a command signal to cause the medication to be delivered to the patient at the revised dosage rate;
   wherein the first control algorithm comprises the following steps:
      comparing a current value of the first vital sign with the target value or range to determine a differential value;
      calculating a dosage adjustment based on the differential value and a drug scalar value; and
      generating the revised dosage rate as a function of the dosage adjustment and the first dosage rate; and
   wherein the control unit is further configured to:
      store the first dosage rate and the revised dosage rate;
      analyze a set of dosage rates of the medication for the patient; and
      generate an alarm command if a rate of change of the dosage rates over a set time period exceeds a predetermined threshold.

19. The system of claim 18, wherein the first vital sign comprises a mean arterial pressure of the patient, and wherein the first source comprises a transducer attached to the patient.

20. The system of claim 18, wherein the control unit is further configured to generate the revised dosage rate by:
   prior to delivering the medication to the patient according to the revised dosage rate, determining whether a first time period exceeds a minimum time period, wherein the first time period is defined as an elapsed time since a last dosage rate change occurred; and
   if the first time period is less than the minimum time period, setting the revised dosage rate to the first dosage rate;
   if the first time period is greater than the minimum time period, delivering the medication to the patient according to the revised dosage rate; and
   wherein the minimum time period is greater or equal to a line lag.

21. The system of claim 18, wherein the control unit is further configured to:
   receive a minimum dosage rate and a maximum dosage rate;
      determine whether the revised dosage rate is greater than the minimum dosage rate and less than the maximum dosage rate; and
   if not, (i) set the revised dosage rate to the first dosage rate, (ii) maintain the first dosage rate and deliver the medication to the patient according to the first dosage rate, and (iii) generate an alarm command.

22. The system of claim 18, wherein the control unit is further configured to:
   calculate a difference between the revised dosage rate and the first dosage rate prior to delivering the medication to the patient according to the revised dosage rate; and
   if the difference exceeds a limit change threshold, set the revised dosage rate to the limit change threshold plus the first dosage rate.

23. The system of claim 18, wherein the control unit is further configured to:
   receive information concerning the first vital sign from a second source comprising a blood pressure monitor configured to monitor a systolic blood pressure of the patient;
   compare the information received concerning the first vital sign from the first and second sources;
   if the difference between the first vital sign as measured from the first and second sources exceeds a predetermined threshold, generate an alarm command.

24. The system of claim 18, wherein the medication comprises a vasopressor, and wherein the first vital sign comprises a mean arterial pressure of the patient, and wherein the first control algorithm is configured to generate the revised dosage rate to maintain the first vital sign within 5 mmHg of the target value.

25. The system of claim 18, wherein the control unit is further configured to:
   receive a flow rate of a carrier fluid;
   calculate a line lag based on the flow rate of the carrier fluid;
   set a minimum time period equal to the line lag; and
   wherein the step of generating the revised dosage rate further comprises first determining whether a first time period as measured as time elapsed since a last dosage rate change exceeds the minimum time period.

26. The system of claim 18, wherein the control unit is further configured to:
   before generating the revised dosage rate, compare the information concerning a first vital sign to a stored vital sign representing the vital sign prior to receiving the first vital sign; and
   if the first vital sign is equal to the stored vital sign, set the revised dosage rate to the first dosage rate.

* * * * *